(12) United States Patent
Kim

(10) Patent No.: US 7,903,152 B2
(45) Date of Patent: Mar. 8, 2011

(54) MOBILE ENTERTAINMENT AND COMMUNICATION DEVICE

(75) Inventor: Ki Il Kim, Los Angeles, CA (US)

(73) Assignee: Minerva Industries, Inc., Los Angeles, CA (US)

( * ) Notice: Subject to any disclaimer, the term of this patent is extended or adjusted under 35 U.S.C. 154(b) by 7 days.

(21) Appl. No.: 12/435,964

(22) Filed: May 5, 2009

(65) Prior Publication Data

US 2009/0213264 A1 Aug. 27, 2009

Related U.S. Application Data

(60) Division of application No. 10/773,606, filed on Feb. 6, 2004, which is a continuation-in-part of application No. 10/719,363, filed on Nov. 20, 2003, now Pat. No. 7,321,783, which is a continuation of application No. 09/531,356, filed on Mar. 20, 2000, now Pat. No. 6,681,120, which is a continuation-in-part of application No. 08/846,108, filed on Apr. 25, 1997, now Pat. No. 6,278,884.

(51) Int. Cl.
*H04N 5/76* (2006.01)

(52) U.S. Cl. ............ 348/231.99; 348/231.9; 348/207.11; 348/552

(58) Field of Classification Search .. 348/231.99–231.9, 348/207.11, 552; 439/152, 153, 155, 160; 361/684, 736, 737, 740, 741
See application file for complete search history.

(56) References Cited

U.S. PATENT DOCUMENTS

| | | | | |
|---|---|---|---|---|
| 3,779,542 A | * | 12/1973 | Barker et al. | 271/245 |
| 4,301,608 A | * | 11/1981 | Taylor, Jr. | 40/661 |
| 4,857,912 A | * | 8/1989 | Everett et al. | 340/508 |
| 5,299,089 A | * | 3/1994 | Lwee | 361/679.33 |
| 5,491,507 A | | 2/1996 | Umezawa et al. | |
| 5,713,750 A | * | 2/1998 | Ho | 439/159 |
| 5,737,433 A | | 4/1998 | Gardner | |
| 5,874,947 A | * | 2/1999 | Lin | 345/169 |
| 5,889,649 A | * | 3/1999 | Nabetani et al. | 361/679.38 |
| 5,957,718 A | * | 9/1999 | Cheng et al. | 439/347 |
| 5,991,637 A | | 11/1999 | Mack, II et al. | |
| 6,067,460 A | | 5/2000 | Alanara et al. | |
| 6,102,720 A | * | 8/2000 | Tung | 439/159 |
| 6,154,201 A | | 11/2000 | Levin et al. | |
| 6,219,231 B1 | * | 4/2001 | Nabetani et al. | 361/679.32 |
| 6,239,700 B1 | | 5/2001 | Hoffman et al. | |
| 6,343,945 B1 | * | 2/2002 | Liikanen | 439/160 |

(Continued)

*Primary Examiner* — Yogesh K Aggarwal

(74) *Attorney, Agent, or Firm* — Hershkovitz & Associates, LLC; Abraham Hershkovitz

(57) ABSTRACT

A mobile communication device in a palm-held size housing has a cellular or satellite telephone capable of wireless communication with the Internet and remotely located telephones. The device includes one or more replaceable memory card sockets for receiving a blank memory card for recording data directly from the Internet and, in particular, musical performances that then can be selectively reproduced by the device for the enjoyment of the user, including both audio and visual recordings and reproductions. The device also includes a camera and microphone for recording images and sound within the range of the device that can be wirelessly transmitted, either selectively or automatically to a remote telephone. Further, the device includes sensors for sensing unusual conditions that may also be transmitted to a remote telephone, together with the location of the device as determined by a GPS section of the device. Still further the device includes a connectable stethoscope for detecting and transmitting sounds from the chest of a user to a remote location.

3 Claims, 3 Drawing Sheets

U.S. PATENT DOCUMENTS

| | | | |
|---|---|---|---|
| 6,364,674 B1 * | 4/2002 | Kajiura | 439/159 |
| 6,398,567 B1 * | 6/2002 | Nishimura | 439/159 |
| 6,437,797 B1 * | 8/2002 | Ota | 345/638 |
| 6,493,239 B2 * | 12/2002 | Ando et al. | 361/796 |
| 6,747,692 B2 * | 6/2004 | Patel et al. | 348/211.2 |
| 6,961,087 B1 * | 11/2005 | Yoshida | 348/231.1 |
| 7,123,936 B1 | 10/2006 | Rydbeck et al. | |
| 7,321,783 B2 | 1/2008 | Kim | |
| 2001/0011308 A1 * | 8/2001 | Clark et al. | 710/20 |
| 2002/0036236 A1 * | 3/2002 | Kondo et al. | 235/492 |

* cited by examiner

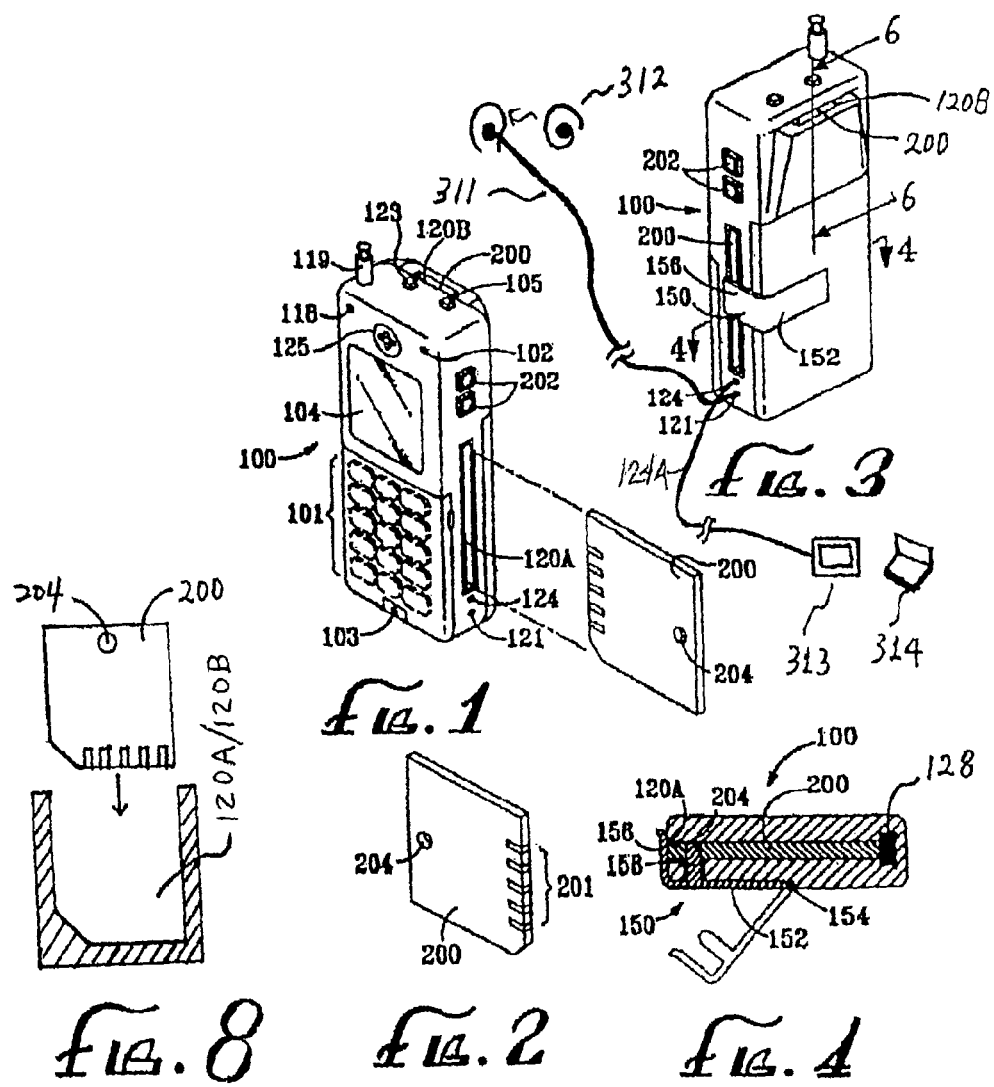

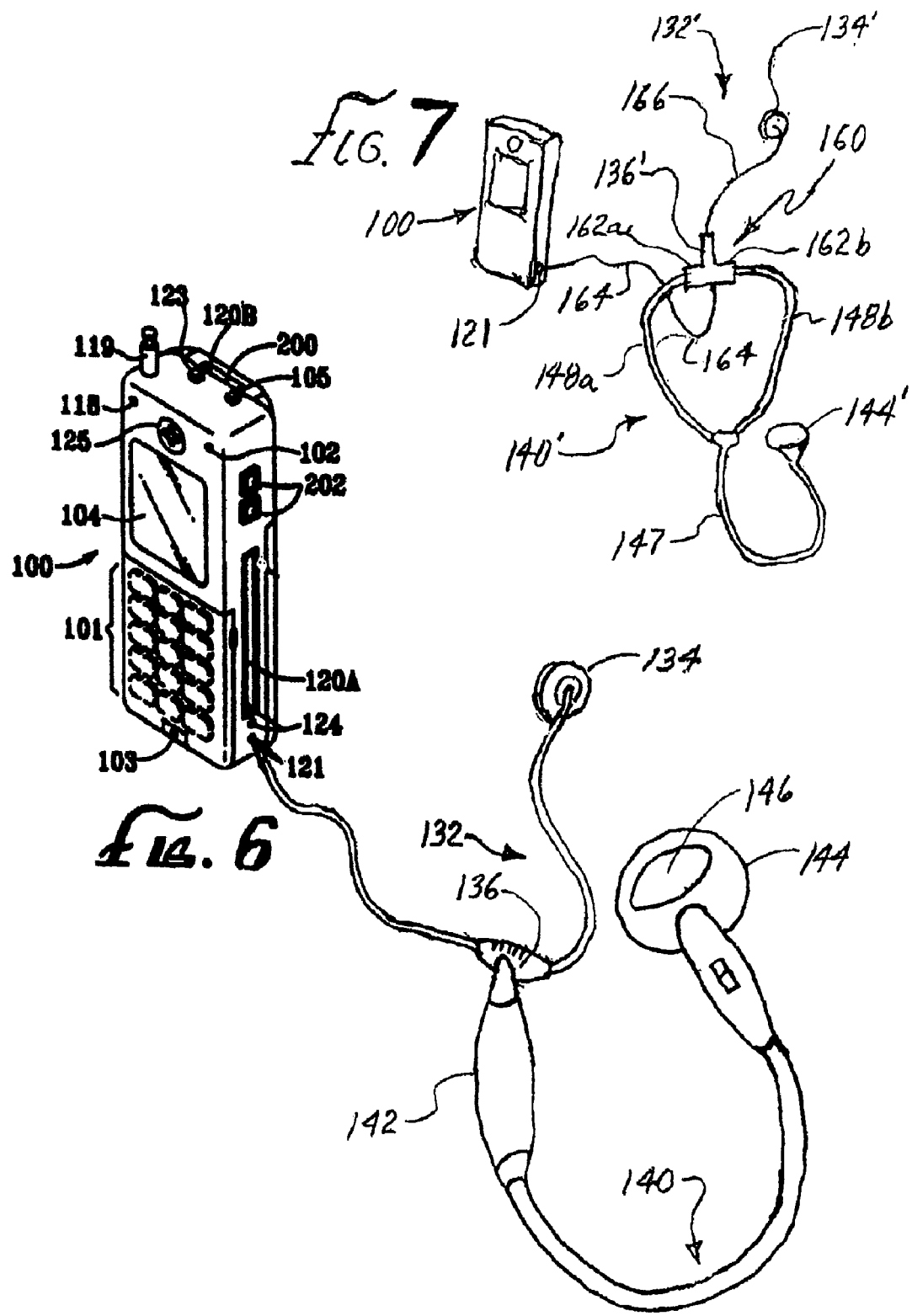

MOBILE ENTERTAINMENT AND COMMUNICATION DEVICE

This is a Divisional Application of application Ser. No. 10/773,606 filed on Feb. 6, 2004, which is a Continuation-In-Part of application Ser. No. 10/719,363, filed Nov. 20, 2003, now U.S. Pat. No. 7,321,783 which is a Continuation of application Ser. No. 09/531,356, filed Mar. 20, 2000, now U.S. Pat. No. 6,681,120, which is a Continuation-In-Part of application Ser. No. 08/846,108, filed Apr. 25, 1997, now U.S. Pat. No. 6,278,884, all of which are incorporated in this Application in full by this reference.

This invention relates to a mobile communication device that is readily carried by a person and provides numerous conveniences and features including, but not limited to, a cellular or satellite telephone with a camera, access to the Internet, and a stethoscope connectable to the telephone for remote patient diagnosis and monitoring.

An object of this invention is to provide a personal communication device that is portable and includes a cellular or satellite accessible telephone with the ability to access the internet, replaceable memory cards for downloading data from the internet, and means for reproducing such data on the device from the cards. Specifically, the device of this invention is particularly adapted to download music, images or other data in a wireless manner from the Internet and selectively reproduce such music, images or other data from replaceable memory cards for one's personal enjoyment or other use.

Still another object of the present invention is to provide a mobile communication device that wirelessly records data from the Internet and selectively reproduces that data, such as music and/or images, and also provides a portable security device capable of automatically communicating with a remote telephone and transmitting emergency data including sounds, pictures, location and similar information when selectively activated by the owner or when automatically activated by conditions sensed by integral sensors, including conditions such as sudden movement, sounds, light, heat, smoke or the like, including being activated from a remote location by a telephone call to initiate a signal or a vibrator to turn on the camera and microphone.

A still further object of this invention is to provide a remote medical diagnostic system by using the communication device to transmit images and sounds from a patient using the device to a remotely located doctor or other medical professionals. Specifically, by this system a stethoscope is selectively connected to the communication device and with the camera and cellphone activated the doctor can listen to the user's lungs and heart as the stethoscope is positioned by the user under the direction of the doctor.

Other and more detailed objects and advantages of the present invention will readily appear to those skilled in the art from the detailed description and accompanying drawings of the preferred embodiments, wherein:

FIG. 1 is a perspective view of the front of the communication device of the present invention;

FIG. 2 is a perspective view of a replaceable memory card for use with the device illustrated in FIG. 1;

FIG. 3 is a perspective view of the back of the device of the present invention showing an optional card latching device;

FIG. 4 is a sectional view of the device taken on the line 4-4 in FIG. 3;

FIG. 6 is a perspective view of the communication device with the stethoscope connected through a headset;

FIG. 7 is a perspective view similar to FIG. 6 but illustrating and alternative embodiment; and FIG. 8 is a plan view of one embodiment of the sockets of the entertainment and communication device shown in FIGS. 1 and 3.

Figure 5:
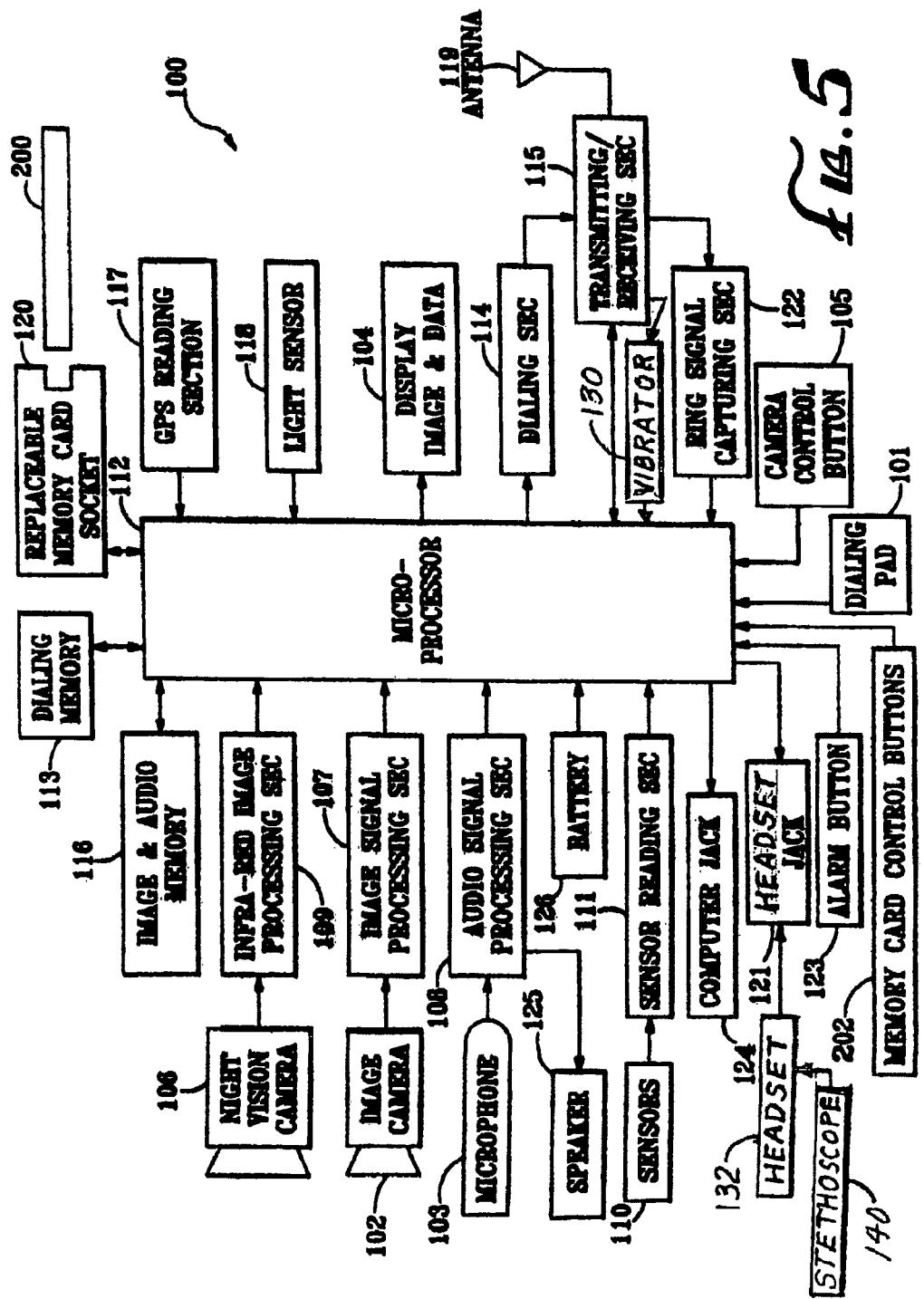
FIG. 5 is a schematic drawing of the components of the communication device shown in FIGS. 1 and 2.

Referring more particularly to the figures, the entertainment and communication device, generally designated 100, includes a cellular telephone or satellite accessible telephone or the like, hereinafter referred to collectively as a "cellphone", having a dialing pad 101 with push buttons for operating the cellphone in a substantially conventional manner and also for controlling the operation of other components of the device 100. The cellphone includes a microphone 103 and a speaker 125 for using the cellphone as a telephone for verbal communications. A display panel 104 is provided on the front of the device 100 for displaying images and data, including but not limited to the conventional data displayed for the use of the cellphone. The cellphone also includes a dialing memory 113, a dialing section 114, a transmitting/receiving section 115, an antenna 119, a vibrator 130 and a ring signal capturing section 122. The microphone 103 and speaker 125 are connected through an audio signal processing section 108 to the microprocessor 112 of the device 100. The dialing memory 113, dialing section 114, transmitting/receiving section 115, vibrator 130, ring signal capturing section 122 and dialing pad 101 are also connected to the microprocessor 112 for operating the cellphone in a conventional manner, through the microprocessor 112.

The cellphone of the entertainment and communication device 100 preferably is of the type that is capable of making a wireless connection to the Internet for receiving data therefrom and transmitting data thereto, such as the Samsung.RTM. Model No. 3500, Qualcom.RTM. No. 1960, Sprint-.RTM. PCS, or the like, without a hardwire connection through a personal computer or telephone line.

The entertainment and communication device 100 of the present invention preferably is provided with a socket 120 for receiving a replaceable memory card 200. The opening for the socket 120 may be provided on the side of the device 100, as shown at 120A, or at one end of the device 100, as shown at 120B, or both. The memory card 200 is provided with electrical contacts 201 (see FIG. 2) which are adapted to engage corresponding electrical contacts (not shown) in the socket 120, which contacts in turn are connected to the microprocessor 112 for communication between the replaceable memory card 200 and the microprocessor 112. The memory card 200 may be a prerecorded card or a flash (blank) card suitable for recording data from the microprocessor 112. By appropriately operating the cellphone to connect to or access the Internet and then operating the memory card control buttons 202, data from the Internet may be recorded on the replaceable memory card 200, such as musical performances, images (still or moving), written text or the like (hereinafter referred to as "data"). In addition to the audio data, the musical performance data from the Internet may include images of the performers or the like, and/or the words of the musical performance. Other audio and visual data also may be downloaded from the Internet to memory card 200. Subsequent to the recordation of the musical performance or other data on the replaceable memory card 200 or upon the positioning of a prerecorded memory card 200 in a socket 120, the memory card control buttons 202 may be manipulated to reproduce the musical performance or other data with the sound being broadcast by the speaker 125 or to earphones 311 or headset 132 (FIG. 6) connected to the headset jack 121 or transmitted to wireless earphones 312. The device 100 also includes controls, such as on dialing pad 101 or separately, for controlling the music volume, balance, selection (skip), equalization and the like. The images and/or words included in the recording on a memory card 200 will be displayed on the display panel 104.

The memory card 200 is preferably of a high memory capacity and a size to fit substantially inside the housing of the device 100 so as not to protrude therefrom and yet be of substantially the full width of the device 100 to maximize the memory capacity of the card 200 substantially beyond the memory capacity of conventional prerecorded memory cards, such as for MP3 players. Of course, the width of the device 100 is limited from a practical standpoint to a width that is comfortable in the palm of an adult person's hand for use as a telephone. Thus, as a practical matter, the width of the memory card is limited to about 1½" to 2". Similarly, the overall size of the device 100 must be sufficiently small to be comfortably carried in a pocket or purse to be most practical. Further, while the thickness of the card 200 may be increased somewhat for increasing the memory capacity there is also a practical limit to that increased thickness so that the thickness of the device 100 does not become excessive, but it is contemplated that memory cards 200 of about twice the thickness may be provided and interchangeably installed in the socket 120 for at least doubling the memory capacity or separate sockets, such as sockets 120A and 120B, may be provided for accommodating memory cards 200 of different thicknesses. Still further, the length of the device 100 is limited to a practical length and, therefore, the vertical length of the card is similarly limited. The card 200 and socket 120 may be provided with matching non-symmetrical shapes, grooves, ridges or the like for requiring the card 200 to be inserted into the socket in the correct orientation, such as the cutoff corner of card 200 shown in FIG. 1 (lower left) and FIG. 2 (lower right). The device 100 may also be provided with an integral image and audio storage memory 116 connected to the microprocessor for temporary or permanent storage of data, in addition to data storage on cards 200, and the data stored on memory 116 may be reproduced in the same manner as from replaceable memory cards 200.

Referring more particularly to FIGS. 3, 4 and 8, a latching device, generally designated 150, is shown for retaining the replaceable memory card 200 in the socket 120A and for facilitating the removal of the memory card 200 from the socket 120A. The latching device 150 includes a lever 152 pivotally connected at 154 to the back of the housing of the device 100, with a tab 156 extending along the side of the device and over a portion of the socket 120A in the closed position. A pin 158 extends inwardly from the lever 152 and engages a hole 204 in the memory card 200. When the latching device 150 is pivoted to the open position shown in dashed lines in FIG. 4, the memory card 200 may be readily removed from socket 120A by placing a finger on the portion of the card 200 exposed by opening the latching device 150, or by engaging the hole 204 with a finger nail or a pointed implement, such as a pencil or pen. Further, the pin 158 and hole can be sized and relatively positioned such that the pin 158 urges the card 200 outwardly upon opening the latching device. Still further, the socket 120A/120B may be provided with a spring 128 for urging the card 200 outwardly as soon as the card is unlatched. Of course, either the tab 156 or pin 158 may be omitted because the other (pin or tab, respectively) will retain the card 200 in the socket 120A. The latching device 150 may be of a width to only cover a portion of the socket 120A, as shown, or of a width to cover the entire socket (not shown).

Since the device 100 can be wirelessly connected to the internet, it is also possible to use the device 100 for any other Internet functions, such as sending and receiving e-mail, conducting ebusiness, etc. Further, in view of the recording capability of the device 100, the telephone conversations on the cellphone may be selectively recorded (one or both sides) and the device can be used for any sound recording, such as for dictation or face-to-face conversations or conferences. Still further, the microprocessor 112 includes means for automatically interrupting the playing of any musical performance being reproduced on the device 100 when a telephone call is placed or received on the cellphone until the call is completed.

All of the aforedescribed functions and those described hereinafter are powered by a battery 126 in the device 100 which preferably is a single rechargeable battery.

The device 100 is also provided with a computer jack 124 connected to the microprocessor for selectively connecting the device 100 directly to a computer 314, radio, television 313 or CD, DVD, VCR, tape or phonograph record player (not shown) by a hard wire 124A for downloading and uploading (where appropriate) to and from the replaceable memory card 200 or fixed memory 116 in the device 100.

The device 100 is also provided with various other features for the personal entertainment, communication, security, safety, diagnosis, monitoring and the like of the person at all times that the person has the device 100 with him or her. A video camera 102 is connected through an image signal processing section 107 to the microprocessor 112 and the camera operation is controlled by button 105, whereby images may be displayed on the panel 104, recorded on either the integral memory 116 or the replaceable memory card 200, or transmitted by the cellphone to a remote telephone which may be located at a police station, security office, one's own personal computer or the like. The video camera 102 is preferably a digital camera for electronically capturing images, either still or moving, for minimizing the size and battery power requirements, but also may be an analog type camera. Similarly, an infrared night vision camera 106 may be provided and connected to the microprocessor 112 through an infrared image processing section 109 to record or transmit images in the same manner as video camera 102, and a light sensor 118 is connected to the microprocessor 112 for automatically selecting the operation of the night vision camera 106 when the ambient light is at a very low level. Cameras 102 and 106 will be referred to generically as a "camera". The microphone 103 may also be activated manually or automatically by the microprocessor 112 when either of the cameras 102 or 106 are activated for recording and/or transmitting sounds within the range of the device 100 synchronously with the recording or transmission of images by one of the cameras.

The device 100 also includes various emergency features for use by the person carrying the device. An alarm button 123 is provided and may be activated to produce an audible alarm from the speaker 125 for dissuading an attacker or intruder or activating a silent alarm whereby the cellphone is automatically operated to communicate the emergency condition to a remote telephone, such as by dialing "911" or a private security telephone number or the like. Similarly, one or more sensors 110, such as motion, infrared, ultrasonic, acceleration, sound, light, heat, smoke, carbon monoxide, poisonous gas or the like sensors, are provided with the device 100 and selectively activated for providing either an audible or silent alarm, similar to the functions of the panic alarm button 123 but without requiring operator activation, and the sensors 110 are connected through the sensor reading section 111 to the microprocessor 112 for using any of the functions of the device 100. For example, with the acceleration sensor of sensors 110 activated while a person has the device 100 in an automobile, the sudden deceleration of the automobile in an accident condition would be sensed by the acceleration sensor to cause the microprocessor 112 to dial an appropriate telephone number stored in the dialing memory 113, such as a "911" or a vehicle rescue number, and transmit the emergency as well as the location of the device 100 as determined by a global positioning satellite (GPS) reading section 117 provided with the device, which GPS reading section 117 may also be activated by the panic alarm 123. Further, if the motion sensor or similar sensors 110 are activated and the device 100 is appropriately positioned, for example in a hotel room, the motion and/or presence of an intruder will be sensed and communicated through the sensor reading section 111 to the microprocessor 112 to activate any desired function, such as an audible alarm from the speaker 125, an automatic dialing of a "911" number, operation of electronic camera 102 or infrared camera 106, operation of the microphone 103, operation of the GPS reading section 117 or the like. Similar functions can be performed by the device 100 when any of the other sensors are activated to sense a particular condition, such as heat, smoke, carbon monoxide, poisonous gas or the like.

The device 100 may also be used as a remote security or observation device to be activated upon demand though the cellphone function. For example, the device 100 may be appropriately positioned and left in a home, office or plant and subsequently the user may dial the cellphone which, through either a silent answering function or the vibrator 130 being sensed by a motion sensor 110, activates the camera 102 or 106 to provide a visual image of the area and/or the microphone 103 to receive the sounds in the area. Those images and/or sounds may be transmitted by the cellphone in real time to the caller or to a computer, a police station, security office or the like. Those images and/or sounds may be recorded on the internal memory 116 or a memory card 200 in addition to or as an alternative to transmitting same by the cellphone function.

Referring more specifically to FIG. 6, a still further function of the device 100 is illustrated. The headset 132 is provided with an earpiece 134 which may be a single piece or dual pieces (not shown) having a speaker(s) and a microphone 136. When the headset 132 is plugged into a headset jack 121, as shown, the cellphone may be used in a hands-free manner or, for example, the user may listen to music from the memorys 116 or 200. Further, a stethoscope 140 is provided that has an adapter 142 for connecting to the microphone 136 of the headset 132 and a chestpiece 144 for pressing to the chest or back of a person or animal that is being examined. The sounds sensed by the chestpiece 144 are received by the microphone 136 and transferred to the device 100, where such sounds may be recorded by memorys 116 and 200 and/or transmitted by the cellphone, for example, to a doctor that is examining or monitoring the user of the device 100 from a remote location or to the Internet for subsequent use. Also, the camera 102 may be activated and images transmitted to the doctor or recorded for subsequent evaluation. The stethoscope may be a conventional manual device, thereby relying on the microphone 136 to pick-up the sounds, or an amplified stethoscope such as the 3M Littmann.RTM. Electronic Stethoscope that produces either the sounds or an electronic signal that can be directly supplied to the device 100 for reproducing the amplified sounds and other data. The electronic stethoscope chestpiece 144 also may have a LCD display 146 and a battery for operating the electronics. As an alternative, the electronic stethoscope may be provided with a plug for connecting directly to the headset jack 121 and appropriate electronic circuitry, such as in adaptor 142, for communicating signals of the sounds to the cellphone for transmission. Further, other medical sensing devices may be provided for plugging into the microphone 136 or directly into the headset jack 121 for providing information concerning the user's condition to a remotely located doctor.

Referring now more specifically to FIG. 7, an alternative arrangement is shown for using a conventional, manual stethoscope 140' with the communication device 100 without modifying or disassembling the stethoscope. A conventional stethoscope 140' typically has a flexible tube 147 leading from a chestpiece 144' to a pair of rigid tubes 148a and 148b having soft earpieces (not shown) at their ends for inserting in a person's ears. By the present invention a T- or Y-shaped audio assembly 160 is provided as a portion of the headset 132' and has a pair of microphones 162a and 162b that are detachably mounted on or to the earpiece ends of the rigid tubes 148a and 148b, respectively, of the stethoscope. A third microphone 136' is provided on the assembly 160 with the two microphones 162a and 162b. A wire 164 connects the assembly 160 to a headset plug for plugging into the headset jack 121 of the device 100. Another wire 166 connects the assembly 160 to the third microphone 136' and earpiece 134' may be used by a person, with or without the stethoscope 140', when operating the device 100. The sounds detected by microphones 162a and 162b from the chestpiece 144' through flexible tube 147 and rigid tubes 148a and 148b thus are transmitted to the communication device for retransmitting by the cellphone portion or recording in the memory 116 or 200, similar to the embodiment of FIG. 6. As a simplified alternative, a single microphone may be provided in assembly 160 with means for receiving the sounds from the two rigid tubes 148a and 148b and/or the person rather than three microphones. Other configurations of the audio assembly 160 also may be used. As noted above with respect to the embodiment of FIG. 6, other medical sensing devices may be used with this T- or Y-shaped audio assembly 160.

The embodiments of FIGS. 6 and 7 also may be used with a laptop or notebook computer for wireless communication or storage rather than the communication device 100 or with a Personal Computer for wired communication.

The device 100 also may be used for paperless prescriptions by doctors by the doctor telephoning the cellphone of device 100 and entering a prescription that may be displayed on the screen 104 with appropriate security measures, such as the doctor's number and picture (if the doctor has a similar cellphone with a camera) or even a signature. By merely displaying the information at a pharmacy or downloading the information onto the pharmacy's computer or printer, the prescription maybe filled.

Thus, by this invention a palm-sized device provides wireless communication for medical diagnosis and monitoring by providing a stethoscope connectable to the cellphone and a camera for the user to transmit and/or record medical information for real time or subsequent use, and numerous other communication, entertainment, security, safety and similar functions are selectively available to the user.

What is claimed is:

1. A digital camera comprising:
   a palm-sized housing that fits in a hand;
   at least one of (1) a built-in microphone, (2) a wired microphone, or (3) a GPS;
   at least one of (1) a wired or wireless earphone, (2) a built-in speaker, or (3) a display;
   a jack for a wired connector to one of a computer or a television;
   a replaceable flash memory card configured to store data captured by at least one of the (1) digital camera, (2) built-in microphone, (3) wired microphone, or (4) GPS and to reproduce the stored data by at least one of the (1) wired or wireless earphone, (2) built-in speaker, (3) display, (4) computer, or (5) television;

the memory card comprising at least one engagement feature without an elastic member or element on the memory card;

the memory card being asymmetrically shaped;

the stored data comprising one or more of sounds, real-time moving images, combined sounds and moving images, combined text and sounds, still images, and GPS location information with or without images;

a socket in the housing for directly receiving longitudinally the memory card without a separate card adapter case or card locking elastic member in the housing, the socket comprising an internal engagement element and a spring disposed in the socket;

the engagement element comprising a latching device including a lever pivotally connected to the housing, wherein the engagement element of the socket mates with the engagement feature of the memory card when the memory card is fully inserted in the socket and secures the memory card in the socket, with the spring facilitating removal of the memory card from the socket by spring power;

the socket being asymmetrically shaped at least at one corner of the socket for preventing incorrect insertion of the memory card;

the socket selectively receiving the memory card;

the socket and the memory card being operatively connected to a microprocessor and at least one of the microphone, the wired microphone, the earphone, the display, the camera, the GPS or the jack; and the microprocessor being configured to at least one of, capture, record, reproduce or transfer data to and from the memory card.

2. A palm hand held electronic device in a housing, the device comprising:

a replaceable flash memory card and a socket in the housing;

a digital camera in the housing;

a microphone;

the flash memory card configured to store data captured by the digital camera and the microphone;

the flash memory card having at least one engagement feature without an elastic member or element on the flash memory card;

the socket being asymmetrically shaped at least at one corner of the socket for preventing incorrect insertion of the flash memory card;

the socket being configured to receive the flash memory card directly without a separate card adapter case or a separate card carrier, wherein the socket is configured to selectively receive the flash memory card;

the socket comprising an internal engagement element comprising a latching device including a lever pivotally connected to the housing, wherein the engagement element is configured for retaining the flash memory card fully within the socket;

a spring disposed in the socket for removing the flash memory card when the flash memory card is entirely positioned in the socket, wherein asymmetrical shapes of the flash memory card and of the socket mate each other in the socket, and wherein the spring facilitates the automatic removal of the flash memory card from the socket by spring power;

the socket being configured to receive and eject the flash memory card longitudinally to and from the socket without controls external to the socket;

the stored data comprising at least one of still images, real time moving images, or combined sounds and moving images; and the socket and the flash memory card being operatively connected to a microprocessor, the microphone and the digital camera to store the data captured by the digital camera and the microphone to the memory card.

3. An electronic device in a housing, the device comprising:

a replaceable flash memory card and a socket in the housing;

at least one of (1) a digital camera capturing still and moving images, (2) a GPS, or (3) a microphone;

the flash memory card being configured to store data captured by at least one of the (1) digital camera, (2) the GPS, or (3) the microphone;

the flash memory card having at least one of an engagement feature without an elastic member or element on the flash memory card and being directly inserted into the socket without a separate card adapter case, the socket being configured to receive and eject the flash memory card longitudinally to and from the socket without controls external to the socket;

the socket being asymmetrically shaped at least at one corner for preventing incorrect insertion of the flash memory card;

the socket being configured to receive the flash memory card directly without a separate card adapter case or a separate card carrier, wherein the socket is configured to selectively receive the flash memory card;

the stored data comprising at least one of sounds, real time moving images, combined sounds and moving images, or GPS location information with or without images;

the socket comprising an internal engagement element comprising a latching device including a lever pivotally connected to the housing, wherein the engagement element is configured for retaining the flash memory card fully within the socket, when the flash memory card is entirely positioned in the socket due to asymmetrical shapes of the socket and the flash memory card mating each other in the socket;

a spring disposed in the socket for removing the card from the socket, wherein the spring facilitates automatic removal of the flash memory card from the socket by spring power; and the socket and the flash memory card being operatively connected to a microprocessor and at least one of the microphone, the digital camera, a sensor or the GPS to selectively store the data captured by at least one of the (1) digital camera, (2) the GPS, or (3) the microphone.

* * * * *